(12) United States Patent
Schafer et al.

(10) Patent No.: US 10,736,590 B2
(45) Date of Patent: Aug. 11, 2020

(54) SPECTRAL PROJECTION EXTENSION

(71) Applicant: KONINKLIJKE PHILIPS N.V., Eindhoven (NL)

(72) Inventors: Dirk Schafer, Hamburg (DE); Michael Grass, Buchholz In der Nordheide (DE); Thomas Koehler, Norderstedt (DE); Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 517 days.

(21) Appl. No.: 15/509,042

(22) PCT Filed: Sep. 16, 2015

(86) PCT No.: PCT/IB2015/057119
§ 371 (c)(1),
(2) Date: Mar. 6, 2017

(87) PCT Pub. No.: WO2016/042491
PCT Pub. Date: Mar. 24, 2016

(65) Prior Publication Data
US 2017/0273647 A1    Sep. 28, 2017

Related U.S. Application Data

(60) Provisional application No. 62/052,506, filed on Sep. 19, 2014.

(51) Int. Cl.
*A61B 6/03* (2006.01)
*A61B 6/00* (2006.01)
*G01N 23/046* (2018.01)

(52) U.S. Cl.
CPC ............ *A61B 6/4241* (2013.01); *A61B 6/032* (2013.01); *A61B 6/482* (2013.01); *A61B 6/5205* (2013.01); *G01N 23/046* (2013.01)

(58) Field of Classification Search
None
See application file for complete search history.

(56) References Cited

U.S. PATENT DOCUMENTS

| 7,105,828 B2 | 9/2006 | Unger |
| 7,272,429 B2 * | 9/2007 | Walker .................. A61B 6/032 378/4 |

(Continued)

FOREIGN PATENT DOCUMENTS

WO    2010/136911    12/2010

OTHER PUBLICATIONS

Li, et al., "Spectral CT Imaging with Hybrid Detectors in Integrating and Dynamic-threshold Counting Modes"; 2013 IEEE Nuclear Science Symposium and Medical Imaging Conference.

(Continued)

*Primary Examiner* — Thomas R Artman
(74) *Attorney, Agent, or Firm* — Larry Liberchuk (57) ABSTRACT

A method includes receiving radiation with a hybrid data detection system of an imaging system. The hybrid data detection system includes a hybrid data detector array with a set of spectral detectors and a set of integrating detectors that are arranged along a transverse axis of an examination region. The method further includes generating a set of truncated spectral projections with the first set of spectral detectors. The method further includes estimating a set of spectral projections for the integrating detectors. The method further includes combining the set of truncated spectral projections and the estimated set of spectral projections. The method further includes estimating a set of spectral projections based on the combined set to produce a complete set of spectral projections. The method further includes processing the complete set of spectral projections to generate volumetric image data.

19 Claims, 5 Drawing Sheets

(56) References Cited

U.S. PATENT DOCUMENTS

| | | | |
|---|---|---|---|
| 7,372,934 B2 | 5/2008 | De Man | |
| 7,433,443 B1 | 10/2008 | Tkaczyk | |
| 7,466,793 B2 | 12/2008 | Wu | |
| 7,995,702 B2* | 8/2011 | Xu | G01N 23/046 378/4 |
| 8,055,050 B2 | 11/2011 | Roessl | |
| 9,159,462 B2* | 10/2015 | Rossl | A61B 6/032 |
| 9,247,919 B2* | 2/2016 | Goshen | G06T 11/005 |
| 10,143,434 B2* | 12/2018 | Proksa | G01T 1/36 |
| 2004/0102688 A1* | 5/2004 | Walker | A61B 6/032 600/407 |
| 2006/0104407 A1 | 5/2006 | Zamyatin | |
| 2007/0147574 A1* | 6/2007 | Bernard De Man | A61B 6/032 378/4 |
| 2007/0205367 A1 | 9/2007 | Deman | |
| 2009/0134337 A1 | 5/2009 | Russ | |
| 2011/0052022 A1* | 3/2011 | Xu | G01N 23/046 382/131 |
| 2012/0057670 A1 | 3/2012 | Luhta | |
| 2013/0308745 A1* | 11/2013 | Goshen | G06T 11/005 378/5 |
| 2013/0329851 A1 | 12/2013 | Rossl | |
| 2017/0079605 A1* | 3/2017 | Proksa | G01T 1/36 |
| 2017/0273647 A1* | 9/2017 | Schafer | A61B 6/032 |

OTHER PUBLICATIONS

Cho, et al., "Cone-beam CT for radiotherapy applications", Physics in Medicine and Biology, vol. 40, No. 11, Nov. 1, 1995.

Schäfer et al., "FBP and BPF reconstruction methods for circular X-ray tomography with off-center detector," Med. Phys. vol. 38 (7), S85-S94, 2011.

Zamyatin et al., "Helical cone beam CT with an asymmetrical detector," Med. Phys. 32, 3117-3127 2005.

\* cited by examiner

SPECTRAL PROJECTION EXTENSION

CROSS REFERENCE TO RELATED APPLICATIONS

This application is the U.S. National Phase application under 35 U.S.C. § 371 of International Application No. PCT/IB2015/057119, filed Sep. 16, 2015, published as WO 2016/042491 on Mar. 24, 2016, which claims the benefit of U.S. Provisional Patent Application No. 62/052,056 filed Sep. 19, 2014. These applications are hereby incorporated by reference herein.

FIELD OF THE INVENTION

The following generally relates to processing spectral projection data and more particularly to extending a set of truncated spectral projections for a detection system that includes both spectral and non-spectral detectors, and is described with particular application to computed tomography (CT). However, the following is also amenable to flat panel, x-ray, radiotherapy and/or other imaging applications.

BACKGROUND OF THE INVENTION

Spectral detectors have a relatively high cost compared to energy integrating detectors. To reduce cost, a detection system may include a hybrid detector array with both spectral detectors and energy integrating detectors, instead of all spectral detectors. With one approach, the detector array may be populated asymmetrically with spectral detectors. For example, a first set of the detectors may be spectral detectors with the remaining detector being energy integrating detectors. In this example, where the spectral detectors cover a small field of view but not the entire full field of view, full field of view acquisitions will result in a set of truncated spectral projections.

An approach for extending truncated non-spectral projections for an asymmetric profile is discussed in Cho et al. Phys. Med. Biol. 40, 1995, pp. 1863-1883. With this approach, an asymmetric profile is extended with the complementary (or approximately redundant) line integrals measured at the opposite gantry angle. Suitable image quality can be achieved for small cone angles in axial scanning modes. With larger cone angles (e.g., greater than 1.5 degrees) or higher pitch (e.g., greater than 0.8), the 3D image quality of asymmetrically truncated acquisitions is gradually deteriorated. The former is discussed in Schäfer et al., "FBP and BPF reconstruction methods for circular X-ray tomography with off-center detector," Med. Phys. Vol. 38 (7), S85-S94, 2011, and the latter is discussed in Zamyatin et al., "Helical cone beam CT with an asymmetrical detector," Med. Phys. 32, 3117-3127 2005. In the spectral case, unfortunately, this problem arises for every spectral channel.

SUMMARY OF THE INVENTION

A method includes receiving radiation with a hybrid data detection system of an imaging system. The hybrid data detection system includes a hybrid data detector array with a set of spectral detectors and a set of integrating detectors that are arranged along a transverse axis of an examination region. The method further includes generating a set of truncated spectral projections with the first set of spectral detectors. The method further includes estimating a set of spectral projections for the integrating detectors. The method further includes combining the set of truncated spectral projections and the estimated set of spectral projections. The method further includes estimating a set of spectral projections based on the combined set to produce a complete set of spectral projections. The method further includes processing the complete set of spectral projections to generate volumetric image data.

An imaging system includes a radiation source configured to emit radiation and a hybrid detector array configured to receive radiation. The hybrid detector array includes spectral detectors and integrating detectors. The spectral detectors are arranged asymmetrically with respect to a center region of the hybrid detector array. The spectral detectors generate truncated spectral projections. The imaging system further includes a reconstructor configured to estimate spectral projections for the integrating detectors, combine the truncated spectral projections and the estimated spectral projections to produce a complete set of spectral projections, and processes the complete set of spectral projections to generate volumetric image data.

An apparatus includes a memory configured to store instructions and a processor configured to execute the instructions. The processor, in response to executing the instructions, receives truncated spectral projections and integrating projections from a detector array that includes spectral detectors and integrating detectors, estimates spectral projections for the integrating detectors based on complementary spectral projections of the spectral detectors for the integrating detectors, and combines the truncated spectral projections and the estimated spectral projections to produce a complete set of spectral projections.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
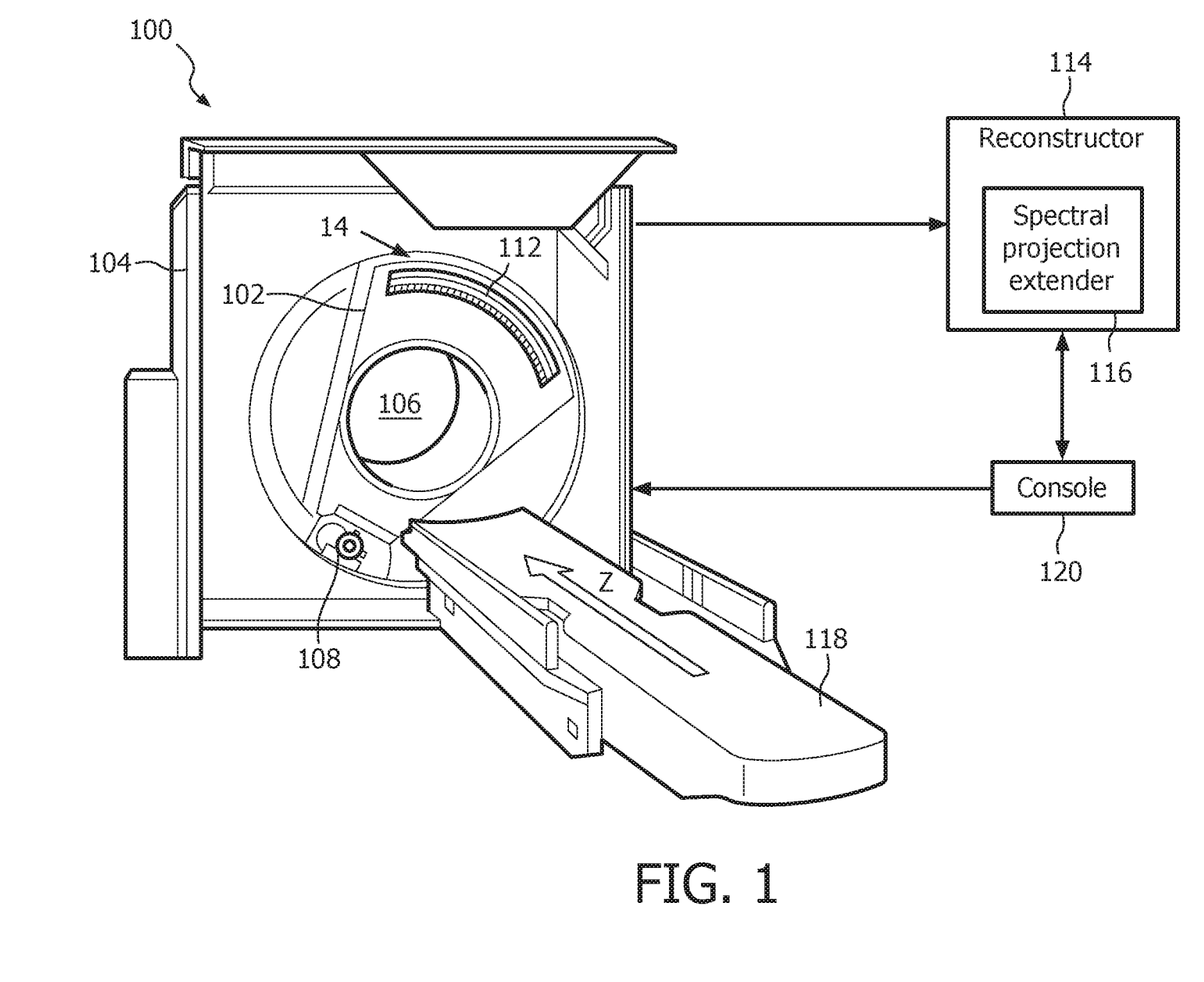
FIG. 1 illustrates an example imaging system with a reconstructor that includes a spectral projection extender.

FIG. 1 schematically illustrates an example imaging system 100, such as a computed tomography (CT) scanner.

The imaging system 100 includes a rotating gantry 102 and a stationary gantry 104. The rotating gantry 102 is rotatably supported by the stationary gantry 104. The rotating gantry 102 is configured to rotate around an examination region 106 about a longitudinal or z-axis. The imaging system 100 further includes a radiation source 108, such as an x-ray tube, that is rotatably supported by the rotating gantry 102. The radiation source 108 rotates with the rotating gantry 102 around the examination region 106 and is configured to emit radiation that traverses the examination region 106.

The imaging system 100 further includes a hybrid detection system 110. The hybrid detection system 110 is located opposite the radiation source 108, across the examination region 106. The hybrid detection system 110 includes a one or two dimensional array 112 with a row or plurality of rows of detectors arranged along the z-axis direction. The one or two dimensional array 112 includes a combination of spectral (multi-energy) detectors and energy integrating (non-spectral) detectors arranged along a transverse (x/y) axis of the examination region 106.

Figure 2:
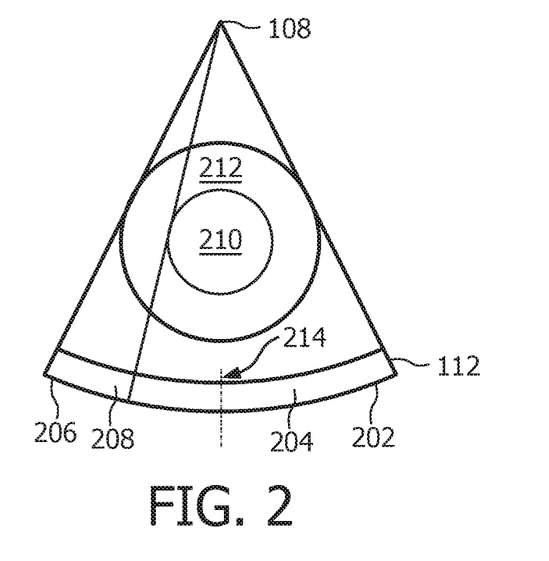
FIG. 2 illustrates an example hybrid detector array with both spectral and energy integrating detectors.
Figure 3:
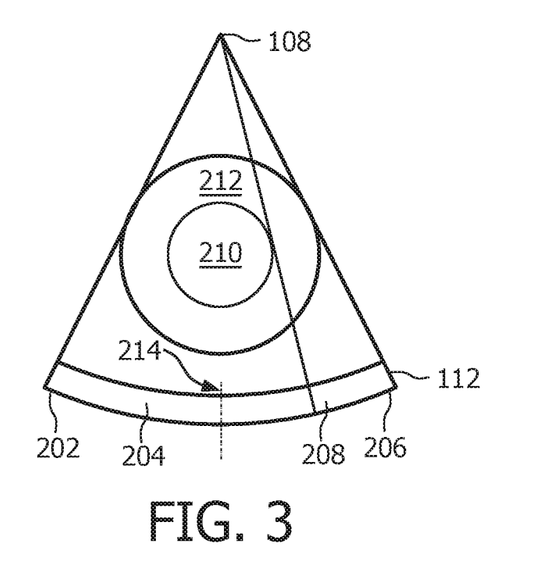
FIG. 3 illustrates another example hybrid detector array with spectral and energy integrating detectors.

FIGS. 2 and 3 show non-limiting examples of the array 112. In FIG. 2, a first detector sub-region 202 from detector array position 1 through detector array position $\alpha X$ is populated with spectral detectors 204, and a second sub-region 206 from detector array position $\alpha X+1$ through detector array position X is populated with energy integrating detectors 208, where X denotes the number of detector elements in a single row and is a positive integer greater than two and $\alpha$ is a percentage less than 100%. In this configuration, the spectral detectors 204 are asymmetrically arranged about a center region 214 of the detector array 112.

In FIG. 2, the first sub-region 202 covers a small field of view (SFOV) 210, e.g., which provides full coverage for a head scan, cardiac scan, etc. The combination of the first sub-region 202 and the second sub-region 206 provides coverage for a large field of view (LFOV) 212, e.g., which provides full coverage for the shoulders, the abdomen, etc. In FIG. 3, the first and second detector sub-regions 202 and 206 are reversed so that the energy integrating detectors 208 span from position 1 to position $\alpha X$ and the spectral detectors 204 span from position $\alpha X+1$ to position X.

With references to FIGS. 1, 2 and 3, the hybrid detection system 110 is configured to operate in a spectral mode and in an energy integrating mode. In energy integrating mode, a complete set of absorption projections are acquired after at least one hundred and eighty degrees (180°) plus a fan angle for the SFOV 210 and the LFOV 212. In spectral mode, a complete set of spectral projections are acquired after at least one hundred and eighty degrees (180°) plus a fan angle for the SFOV 210, but not for the LFOV 212. For the LFOV 212, spectral projections are truncated since spectral projections are missing for the region covered by the second sub-region 206.

With references to FIG. 1, the imaging system 100 further includes a reconstructor 114 that reconstructs projections and generates volumetric data. For spectral LFOV acquisitions, the reconstructor 114 includes a spectral projection extender 116, which estimates spectral projections for the second sub-region 206. The combination of the truncated spectral projections for the first sub-region 202 and the estimated spectral projections for the second sub-region 206 provides a complete set of spectral projections for spectral LFOV acquisitions. As such, the estimated spectral projections extend the truncated spectral projections to generate a complete set of projections for LFOV acquisitions.

As described in greater detail below, in one non-limiting instance, the spectral projection extender 116 estimates the spectral projections for the second sub-region 206 based on complementary spectral projections from the first sub-region 202 and energy integrating measurements from the second sub-region 206. This approach is well suited for asymmetric spectral detector profiles, including for larger cone angles (e.g., greater than 1.5 degrees) in axial scanning and/or higher pitch (e.g., greater than 0.8) for helical scanning, unlike a configuration in which this approach is omitted. The spectral projection extender 116 is not employed for energy integrating mode and SFOV spectral mode.

The reconstructor 114 can be implemented via a processor (s) (e.g., a central processing unit (CPU), a microprocessor, etc.) executing a computer executable instruction(s) embedded or encoded on computer readable storage medium, which excludes transitory medium and includes physical memory and/or other non-transitory medium. The reconstructor 114 can also execute a computer executable instruction(s) carried by transitory medium such as a carrier wave, signal, etc. The reconstructor 114 can be part of the imaging system 100 (as shown) or separate therefrom.

The imaging system 100 further includes a subject support 118, such as a couch, that supports a subject in the examination region 106, for example, before, during and/or after scanning.

The imaging system 100 further includes a computing system, which serves as an operator console 120 and includes a human readable output device such as a monitor and an input device such as a keyboard, mouse, etc. The console 120 allows an operator to interact with the scanner 100 via a graphical user interface (GUI) and/or otherwise. For instance, the user can employ the input device to select an imaging protocol such as an imaging protocol including a LFOV and spectral mode.

In an example general case, a spectral measurement for a detector element includes N different measurements, each for a different energy bin and with a different spectral sensitivity. This can be expressed as shown in EQUATION 1:

$$I_i = \int S_i(E)\psi(E)e^{-\mu(E)}dE. \quad \text{EQUATION 1:}$$

where $I_i$ represents an ith intensity measurement, $S_i(E)$ represents an effective spectral sensitivity for the measurement, $\psi(E)$ is a radiation source energy emission spectrum, and $\mu(E)$ represents an energy dependency of the absorption.

The measured spectral attenuations of the detectors 204 in the sub-region 202 can be denoted as shown in EQUATION 2:

$$I_i^{204} = \int S_i(E)\psi(E)e^{-\mu(E)}dE, \text{ and} \quad \text{EQUATION 2:}$$

the corresponding energy integrating measurement can be denoted as shown in EQUATION 3:

$$I^{204} = \sum_i I_i^{204}. \quad \text{EQUATION 3:}$$

A fraction of every spectral channel can then be calculated as shown in EQUATION 4:

$$f_i^{204} = I_i^{204}/I^{204}. \quad \text{EQUATION 4:}$$

For every energy integrating measurement $I^{208}$ in sub-region 206, the spectral information $I_i^{208}$ can be estimated using the spectral fractions $f_i^{204}$ of the corresponding ray from sub-region 202 as shown in EQUATION 5:

$$I_i^{208} = f_i^{204} I^{208}. \quad \text{EQUATION 5:}$$

Figure 4:
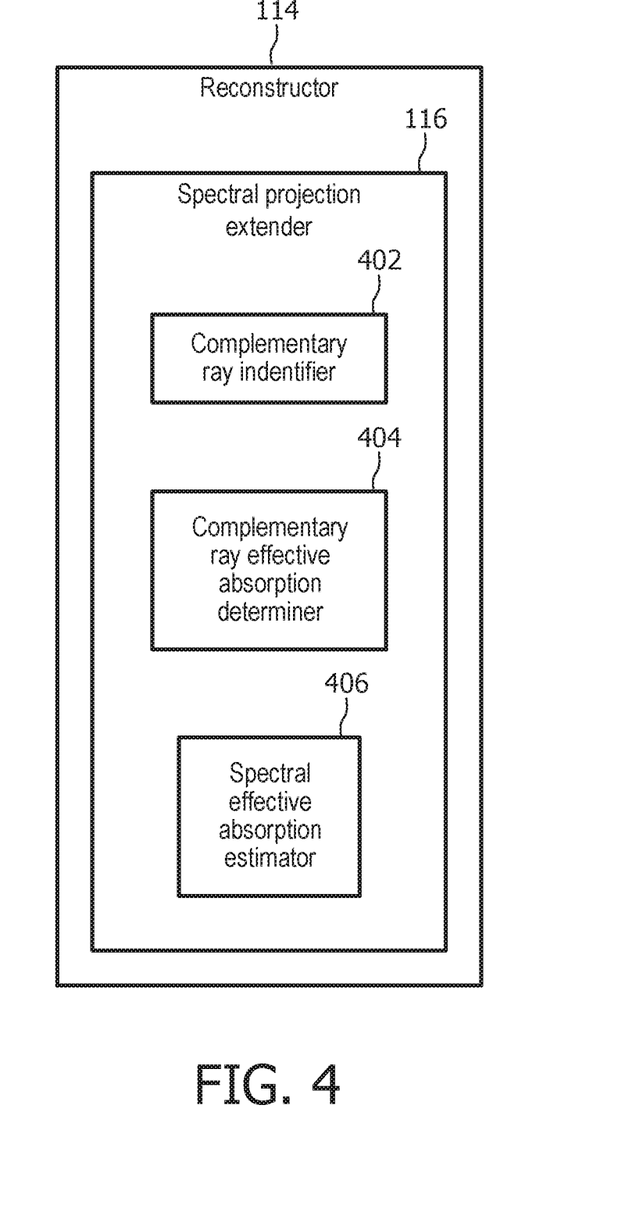
FIG. 4 illustrates an example of the spectral projection extender.

FIG. 4 illustrates an example of the reconstructor 114 and the spectral projection extender 116. In this example, N=2, and the two spectral bins are mapped to photo-electric and Compton scattering bases. In another embodiment, N>2, and the spectral bins can include photo-electric, Compton scattering, and/or other bases.

For the spectral measurements taken by the spectral detectors 204, the reconstructor 114 determines an effective absorption P by the photo-electric effect and an effective absorption C by Compton scattering in a ray based respectively on EQUATIONS 6 and 7:

$$I_L = \int S_L(E)\psi(E)e^{-P\mu_P(E)-C\mu_C(E)}dE, \text{ and} \qquad \text{EQUATION 6:}$$

$$I_H = \int S_H(E)\psi(E)e^{-P\mu_P(E)-C\mu_C(E)}dE, \qquad \text{EQUATION 7:}$$

where $I_L$ and $I_H$ are lower and higher intensity measurements, $\mu_P(E)$ and $\mu_C(E)$ are the energy dependency of the absorption, and $S_L(E)$ and $S_H(E)$ are the effective spectral sensitivity.

The reconstructor 114 determines a non-spectral measurement (equivalent to an energy integrating measurement) for the first sub-region 202 of spectral detectors 204 based respectively on EQUATION 8:

$$I = \int S(E)\psi(E)e^{-P\mu_P(E)-C\mu_C(E)}dE, \qquad \text{EQUATION 8:}$$

where I is the combined (integrating equivalent) measurement and $S(E)=S_H(E)+S_L(E)$. For the second sub-region 206, the reconstructor 114 employs the spectral projection extender 116 to estimate spectral projections. An example of this follows.

Figure 5:
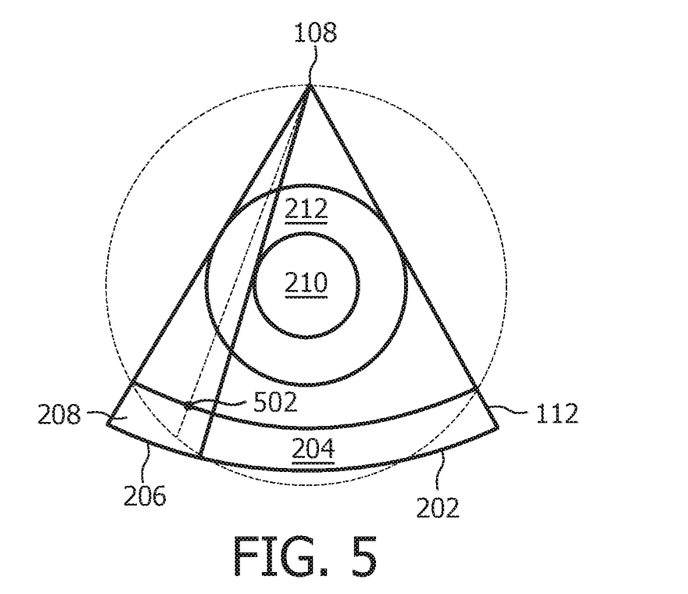
FIG. 5 illustrates an example of a missing projection for the example of the hybrid detector array of FIG. 2.
Figure 6:
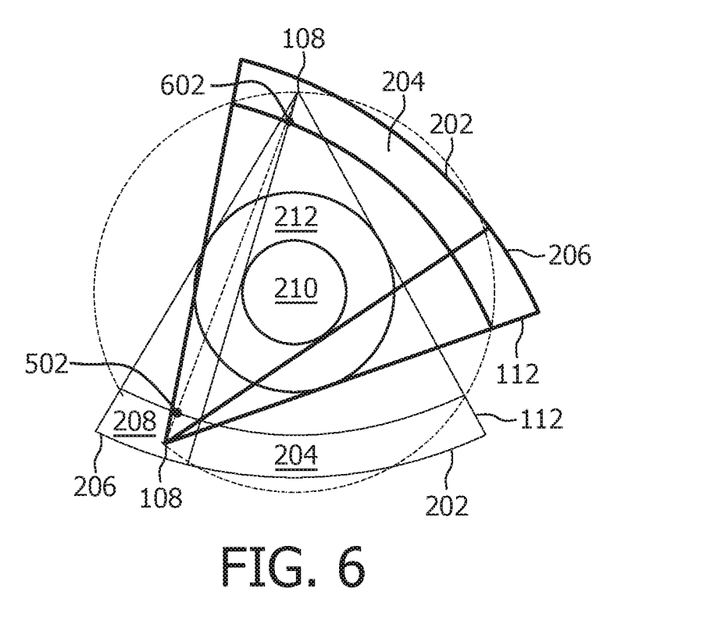
FIG. 6 illustrates an example of a complementary projection for the example of the hybrid detector array of FIG. 2.

The spectral projection extender 116 includes a complementary ray identifier 402 that identifies spectral rays from the first sub-region 202 that are complementary to the integrating rays of the second sub-region 206. In order to clearly distinguish the two rays under consideration, the integrating ray, measured according to EQUATION 8, is referred to herein as the direct ray. Briefly turning to FIG. 5, an example missing spectral measurement 502 for the first sub-region 206 is illustrated. FIG. 6 shows a complementary spectral measurement 602 from the second sub-region 201.

The spectral projection extender 116 further includes a complementary ray effective absorption determiner 404 that determines effective absorptions $P_{cr}$ and $C_{cr}$ by the photo-electric effect and the Compton scattering for the complementary ray. In one instance, the complementary ray effective absorption determiner 404 employs Cho matching. An example of Cho matching is described in Cho et al. Phys. Med. Biol. 40, 1995, pp. 1863-1883.

The Cho matching algorithm identifies the geometrical location of the best matching complementary ray, which is by design of the detector system a ray measured with a dual layer pixel. Thus, the for the complementary ray, the line integral $P_{cr}$ and $C_{cr}$ are available, either directly through decomposition or the geometrical information leads to the correct $I_H$ and $I_L$ and a decomposition is performed on these data.

The spectral projection extender 116 further includes a spectral effective absorption estimator 406 that estimates, for the second sub-region 206, an effective absorption $xP_{cr}$ by the photo-electric effect and an effective absorption $xC_{cr}$ by Compton scattering based on EQUATION 9:

$$I = \int S(E)\psi(E)e^{-xP_{cr}\mu_P(E)-xC_{cr}\mu_C(E)}dE, \qquad \text{EQUATION 9:}$$

where I is a integration measurement, x is a scaling factor, $P_{cr}$ is an effective photo-electric absorption for the complementary ray, and $C_{cr}$ is an effective Compton scatter absorption for the complementary ray.

Using EQUATION 9, the spectral effective absorption estimator 406 determines the scaling factor x to be a value that matches the total absorption to the integrating measurement I (which is now a well-defined problem since there is only one measurement, I, and one parameter to estimate, x). The spectral effective absorption estimator 406 outputs $xP_{cr}$ and $xC_{cr}$ as the estimated effective photo-electric absorption and the estimated effective Compton scatter absorption of the direct ray.

The reconstructor 114 uses the estimated effective absorption $xP_{cr}$ and $xC_{cr}$ as the effective absorption P and C for the LFOV 212 to generate a complete set of spectral data for the LFOV 212. The reconstructor 114 processes the P and C to generate spectral image data for the larger field of view 212.

In a variation, the reconstructor 114 determines only a ratio of $P_{cr}$ to $C_{cr}$ (or vice versa), and not both $P_{cr}$ and $C_{cr}$, and uses the ratio to estimate the missing spectral data.

In another variation, the reconstructor 114 estimates a spectral intensity based on intensity ratios as shown in EQUATIONS 10 and 11:

$$I_H = \frac{I}{I_L^{cr} + I_H^{cr}} I_H^{cr}, \text{ and} \qquad \text{EQUATION 10}$$

$$I_L = \frac{I}{I_L^{cr} + I_H^{cr}} I_L^{cr}, \qquad \text{EQUATION 11}$$

where $I_L^{cr}$ and $I_H^{cr}$ are lower and higher complementary ray intensity measurements. EQUATIONS 10 and 11 are similar to EQUATIONS 4 and 5 for the two bins example.

In another variation, the reconstructor 114 estimates a logarithm of the spectral intensity based on intensity ratios as shown in EQUATIONS 12 and 13:

$$\log(I_H) = \frac{\log(I)}{\log(I_L^{cr}) + \log(I_H^{cr})} \log(I_H^{cr}), \text{ and} \qquad \text{EQUATION 12}$$

$$\log(I_L) = \frac{\log(I)}{\log(I_L^{cr}) + \log(I_H^{cr})} \log(I_L^{cr}). \qquad \text{EQUATION 13}$$

Figure 7:
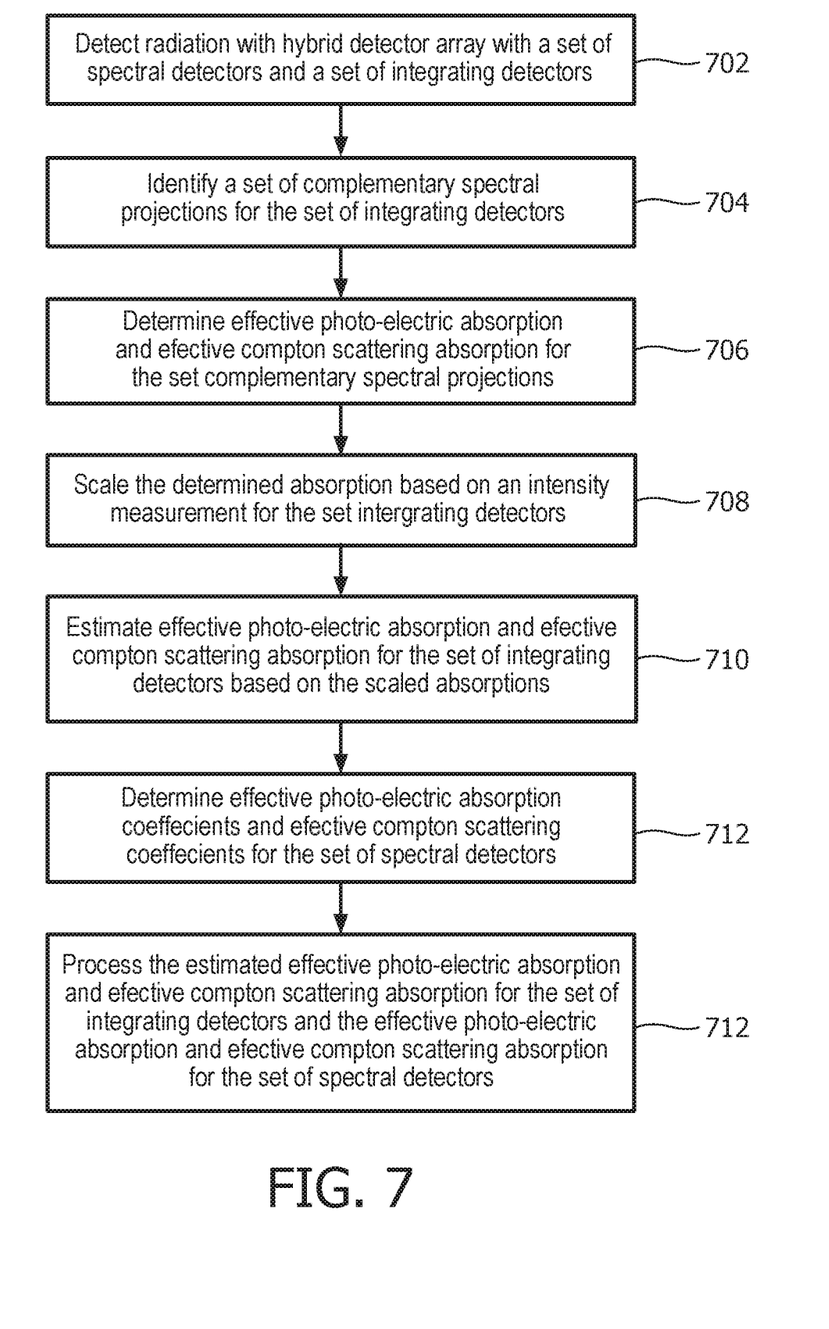
FIG. 7 illustrates a method in accordance with an embodiment described herein.

FIG. 7 illustrates a method in accordance with the embodiments described herein. With this example, N=2 and the two spectral bins are mapped to photo-electric and Compton scattering bases. In another embodiment, N>2, and the spectral bins can include photo-electric, Compton scattering, and/or other bases.

It is to be appreciated that the ordering of the below acts is for explanatory purposes and not limiting. As such, other orderings are also contemplated herein. In addition, one or more of the acts may be omitted and/or one or more other acts may be included.

At 702, radiation emitted by a radiation source of the imaging system is detected by a hybrid detector array, which includes a set of spectral detectors arranged asymmetrically along a detector array and a set of integrating detectors.

At 704, a set of complementary spectral projections of the set of spectral detectors are identified for the set of integrating detectors.

At 706, an effective photo-electric absorption and an effective Compton scattering absorption are determined for the set complementary spectral projections.

At 708, the effective photo-electric absorption and effective Compton scattering absorption for the set complementary spectral projections are scaled based on an intensity measurement of the set of integrating detectors.

At 710, an effective photo-electric absorption and an effective Compton scattering absorption for the set of integrating detectors are estimated based on the scaled effective photo-electric and effective Compton scattering absorptions.

At 712, the effective photo-electric absorption and the effective Compton scattering absorption for the set of spectral detectors are determined.

At 714, the estimated effective photo-electric absorption and effective Compton scattering absorption for the set of integrating detectors and the effective photo-electric absorption and effective Compton scattering absorption for the set of spectral detectors are processed to generate volumetric image data.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for generating image data, comprising:
    receiving radiation by a hybrid data detection system that includes a hybrid data detector array comprising spectral detectors and integrating detectors arranged along a transverse axis of an examination region;
    generating truncated spectral projections by the spectral detectors;
    identifying, for the integrating detectors, complementary spectral projections from the spectral detectors;
    estimating spectral projections for the integrating detectors based on the complementary spectral projections;
    combining the truncated spectral projections and the estimated spectral projections to produce a complete set of spectral projections; and
    generating image data based on the complete set of spectral projections.

2. The method of claim 1, further comprising:
    determining an effective first energy bin absorption and an effective second energy bin absorption for the complementary spectral projections, such that the spectral projections for the integrating detectors are estimated based on the effective first energy bin absorption and the effective second energy bin absorption for the complementary spectral projections.

3. The method of claim 2, wherein the effective first energy bin absorption is an effective photo-electric absorption and the effective second energy bin absorption is an effective Compton scattering absorption.

4. The method of claim 2, further comprising:
    scaling the effective first energy bin absorption and the effective second energy bin absorption for the complementary spectral projections, such that the spectral projections for the integrating detectors are estimated based on the scaled effective first energy bin absorption and the scaled effective second energy bin absorption.

5. The method of claim 4, further comprising:
    estimating the effective first energy bin absorption and the effective second energy bin absorption for the integrating detectors, respectively, as the scaled effective first energy bin absorption and the scaled effective second energy bin absorption.

6. The method of claim 2, further comprising:
    determining a ratio between the effective first energy bin absorption and the effective second energy bin absorption for the complementary spectral projections, such that the spectral projections for the integrating detectors are estimated based on the ratio.

7. The method of claim 6, wherein the effective first energy bin absorptions are effective photo-electric absorptions and the second energy bin absorptions are effective Compton scattering absorptions.

8. The method of claim 6, further comprising:
    scaling the ratio, such that the spectral projections for the integrating detectors are estimated based on the scaled ratios.

9. The method of claim 1, further comprising:
    generating absorption projections for the integrating detectors, such that the spectral projections for the integrating detectors are estimated based on a ratio between the absorption projections and the complementary spectral projections.

10. The method of claim 9, wherein the spectral projections for the integrating detectors are estimated based on the ratio of logarithms between the absorption projections and the complementary spectral projections.

11. The method of claim 1, further comprising:
    employing Cho matching to determine the complementary spectral projections.

12. An imaging system, comprising:
    a radiation source configured to emit radiation;
    a hybrid detector array configured to receive radiation, wherein the hybrid detector array includes spectral detectors and integrating detectors, wherein the spectral detectors are arranged asymmetrically with respect to a center region of the hybrid detector array and generate truncated spectral projections; and
    at least one processor configured to:
        identify, for the integrating detectors, complementary spectral projections from the spectral detectors;
        estimate spectral projections for the integrating detectors based on the complementary spectral projections;
        combine the truncated spectral projections and the estimated spectral projections to produce a complete set of spectral projections; and
        generate image data based on the complete set of spectral projections.

13. The imaging system of claim 12, wherein the spectral detectors produce the complete set of spectral projections for a small field of view and the truncated spectral projections for a large field of view.

14. The imaging system of claim 12, wherein the at least one processor is further configured to:
    determine an effective first energy bin absorption and an effective second energy bin absorption for the complementary spectral projections; and
    scale the effective first energy bin absorption and the second energy bin absorption for the complementary spectral projections, such that the spectral projections for the integrating detectors are estimated based on the scaled effective first energy bin absorption and the scaled effective second energy bin absorption.

15. The imaging system of claim 14, wherein the effective first energy bin absorption is an effective photo-electric absorption and the second energy bin absorption is an effective Compton scattering absorption.

16. The imaging system of claim 12, wherein the at least one processor is further configured to:
    determine a ratio between an effective first energy bin absorption and an effective second energy bin absorption for the complementary spectral projections; and
    scale the ratio, such that the spectral projections for the integrating detectors are estimated based on the scaled ratio.

17. The imaging system of claim 12, wherein the at least one processor is further configured to obtain absorption projections generated by the integrating detectors, such that the spectral projections for the integrating detectors are estimated based on a ratio between the absorption projections and the complementary spectral projections.

18. The imaging system of claim 12, wherein the at least one processor is further configured to obtain absorption projections generated by the integrating detectors, such that the spectral projections for the integrating detectors are estimated based on a ratio of logarithms between the absorption projections and the complementary spectral projections.

19. An imaging apparatus, comprising:
memory configured to store instructions; and
at least one processor configured to execute the instructions, wherein the at least one processor, in response to executing the instructions, causes the imaging apparatus to:
  receive truncated spectral projections and integrating projections from a detector array that includes spectral detectors and integrating detectors;
  identify, for the integrating detectors, complementary spectral projections from the spectral detectors;
  estimate spectral projections for the integrating detectors based on the complementary spectral projections;
  combine the truncated spectral projections and the estimated spectral projections to produce a complete set of spectral projections; and
  generate image data based on the complete set of spectral projections.

* * * * *